(12) United States Patent
Kayser et al.

(10) Patent No.: US 7,615,659 B2
(45) Date of Patent: Nov. 10, 2009

(54) METHOD FOR THE PRODUCTION OF COMPOUNDS CONTAINING PALLADIUM(0)

(75) Inventors: Bernd Kayser, München (DE); Ralf Karch, Kleinostheim (DE); Oliver Briel, Offenbach (DE); Ingo Kleinwächter, Hanau (DE)

(73) Assignee: Umicore AG & Co. KG, Hanau-Wolfgang (DE)

( * ) Notice: Subject to any disclaimer, the term of this patent is extended or adjusted under 35 U.S.C. 154(b) by 484 days.

(21) Appl. No.: 10/533,492

(22) PCT Filed: Oct. 30, 2003

(86) PCT No.: PCT/EP03/12085

§ 371 (c)(1),
(2), (4) Date: Oct. 3, 2005

(87) PCT Pub. No.: WO2004/039819

PCT Pub. Date: May 13, 2004

(65) Prior Publication Data

US 2006/0106239 A1    May 18, 2006

(30) Foreign Application Priority Data

Oct. 31, 2002   (DE) ................. 102 50 901

(51) Int. Cl.
*C07F 15/00*   (2006.01)
*C07F 7/18*    (2006.01)
(52) U.S. Cl. ............................ 556/9; 556/136; 556/137
(58) Field of Classification Search ............ 556/9, 556/136, 137
See application file for complete search history.

(56) References Cited

U.S. PATENT DOCUMENTS 4,098,807 A    7/1978  Stone et al.
6,316,380 B1   11/2001 Nolan et al.

FOREIGN PATENT DOCUMENTS

DE    25 55 374 A1    6/1976
DE    40 20 689 A1    1/1992
DE    100 51 316 A1   4/2002
DE    100 62 577 A1   7/2002
EP    0 508 264 A1   10/1992

OTHER PUBLICATIONS

Krause et al., Organometallics, 11(3), pp. 1158-1167 (1992).*
Krause Jochen et al. "Hepta-1,6-diene and diallyl ether complexes . . . " Chem. Commun., (1998); pp. 1291-1292.
Krause Jochen et al. "1,6-Diene Complexes of Palladium(0) . . . " J. American Chemistry Soc (1999); 121, pp. 9807-9823.
Maria Mendez et al. "Intramolecular Coupling of Allyl Carboxylates . . . " Chem. Eur. J. (2002); 8, No. 16; pp. 3620-3628.
P. W. Jolly et al. "Intermediates in the Palladium-Catalyzed . . . " American Chemical Society, vol. 5, No. 3, (1986); pp. 473-481.
Marcial Moreno-Manas et al. "15 and 30-Membered polyolefinic macrocycles . . . " Tetrahedron 58 (2002); pp. 7769-7774.
Hiroyuki Nakamura et al. "Catalytic Amphiphilic Allylation via Bis . . . " American Cancer Society (2001); pp. 372-377.

* cited by examiner

*Primary Examiner*—Porfirio Nazario Gonzalez
(74) *Attorney, Agent, or Firm*—Robert G. Weilacher; Smith, Gambrell & Russell

(57) ABSTRACT

The present invention relates to a process for preparing a palladium(0) compound, comprising the reaction of a palladium compound with one or more compounds of the general formula I, II or III in the presence of a base:

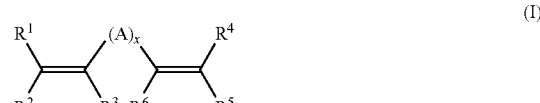

(I)

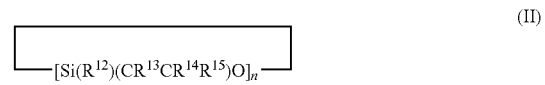

(II)

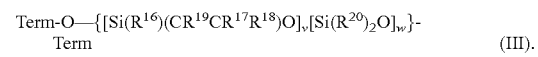

(III).

The Palladium(0) compounds are suitable as homogeneous catalysts, as a precursor for preparing homogeneous catalysts, as a precursor for preparing homogeneous catalysts in situ or as a precursor for preparing heterogeneous catalysts.

22 Claims, No Drawings

METHOD FOR THE PRODUCTION OF COMPOUNDS CONTAINING PALLADIUM(0)

The present invention relates to a process for preparing palladium(0) compounds.

In the form of its compounds, palladium finds use as a catalyst in numerous industrial processes.

More than 80% of the industrially produced chemicals are prepared by catalytic processes. Catalytic processes are generally more economically viable and environmentally friendly than corresponding stoichiometric organic reactions. For the attainment of high yields and selectivities in homogeneous catalytic processes, a wide range of ligand systems has to be used, which in turn requires precursor metal compounds having a wide range of uses. This makes clear the need for constant improvement in the catalyst systems and their preparation processes.

For these applications, one possibility is in particular palladium compounds which contain palladium in the 0 oxidation state. In general, palladium(0) compounds are stabilized by compounds which can provide a free electron pair for coordination. This free electron pair may be provided, for example, by an unsaturated hydrocarbon or by heteroatoms such as phosphorus or nitrogen. Stably storable compounds are commercially obtainable principally only in solid form.

However, compounds which are in liquid form are desired in catalysis. This greatly eases their usability. Often, solid compounds are dissolved in a solvent for this purpose, but solutions of solid Pd(0) compounds are usually unstable and have to be used immediately.

In homogeneous catalysis applications, the precursors used are preferably compounds which can be mixed in a simple manner with ligands, for example different phosphines, so as to be able to prepare a wide range of catalysis systems. This is realized, for example, in the case of the Pd(0) compounds stabilized with unsaturated hydrocarbon ligands.

Numerous Pd(0) complexes with unsaturated compounds in the ligands sphere are known and are described, for example, in Wilkinson, Abel "Comprehensive Organometallic Chemistry", Vol. 6, p. 243ff "Complexes of Palladium(0)".

Pd(0) compounds stabilized by unsaturated hydrocarbons may be differentiated according to the ligands into complexes stabilized by monodentate and by multidentate (chelating) ligands. An example of a Pd(0) complex stabilized by monodentate hydrocarbon ligands is Pd(ethylene)$_3$, which decomposes at room temperature and under air.

Stabler Pd(0) compounds are obtained by chelating, for example bidentate, unsaturated hydrocarbon ligands such as dienes. Dienes are classified according to the separation of the two diene functions into 1,4-diene ligands, 1,5-diene ligands, 1,6-diene ligands, 1,7-diene ligands, etc.

1,4-Diene-stabilized palladium(0) finds wide use as a ligand, for example, in the form of 1,5-diphenyl-1,4-pentadien-3-one (dba). One description of the synthesis is given by M. F. Rettig et al. in Inorg. Synth., 1990, 28. The product is isolated from the synthesis solution as a sparingly soluble precipitate. The solid is substantially air-stable, but solutions in organic solvents of these compounds decompose within hours (STREM catalogue: "Chemicals for research", Catalogue No. 19, 2001-2003).

The use of this complex type as a precursor in homogeneous catalysis is described, for example, in U.S. Pat. No. 6,316,380. In EP-A-508 264, Pd(dba)$_2$ substituted by sulphoalkyl groups is used as homogeneous catalyst in C—C coupling.

A known example of Pd(0) stabilized by 1,5-diene ligand is Pd(COD)$_2$. This is synthesized in DE-A-25 55 374 from Pd(COD)Cl$_2$ in the presence of an organometallic compound, for example Li$_2$(COT)(COT=cyclooctatraene), sodium naphthalide or organoaluminium compounds, in solvents having no active protons. The above patent application also describes the synthesis of Pd(C$_2$H$_4$)$_3$ from Pd(COD)$_2$. Pd(COD)$_2$ is an unstable solid which decomposes within hours under atmospheric conditions. This property makes this compound industrially utilizable only to a limited extent.

J. Krause, G. Cestaric, K.-J. Haack, K. Seevogel, W. Storm, K. R. Pörschke (J. Am. Chem. Soc. 1999, 121, 9807-9823 and Chem. Commun. 1998, 12, 1291) describe the synthesis of molecularly defined hepta-1,6-diene-, diallyl ether- and tetramethyldivinyldisiloxane-palladium(0), which are examples of Pd(0) stabilized by 1,6-diene ligands. The synthesis follows substantially the route described for Pd(COD)$_2$. Oxygen-free solvents have to be used for the synthesis and the materials have decomposition temperatures close to room temperature.

For application in homogeneous catalysis, 1,6-diene-Pd(0)-phosphine and -carbene complexes have been identified. These compounds exhibit high activities in the industrially used Heck reaction and the Suzuki C—C coupling reaction, and are described by M. G. Andreu, A. Zapf, M. Beller in Chem. Comm., 2000, 245 and in DE-A-100 62 577.

In the prior art, 1,4-diene-stabilized Pd(0) compounds are used industrially. These exhibit sufficient stability, but solutions of these compounds are not storage-stable. 1,5- and 1,6-diene-stabilized Pd(0) compounds are distinctly less stable than the 1,4-diene-stabilized Pd(0) compounds. In all diene-stabilized Pd(0) compounds, it is typically necessary to work under inert gas and with dried solvents having no active protons in order to isolate molecularly defined Pd$_2$(diene)$_3$ or Pd(diene)$_2$ compounds. In addition, highly sensitive organolithium compounds which pose potential health risks are used in the synthesis, which makes industrial-scale utilization costly and inconvenient. For this reason, these compound classes have not been used industrially on a large scale to date.

It is therefore an object of the present invention to provide a novel inexpensive process for preparing palladium(0) compounds. Solutions of these compounds should be substantially stable thermally and toward atmospheric conditions. This enables access to economically viable, versatile, novel precursors for applications in homogeneous catalysis, heterogeneous catalysis and complex chemistry.

In particular, the invention relates to a process for preparing a Palladium(0) compound, comprising reaction of a palladium compound with one or more compounds of the general formula (I) in the presence of a base:

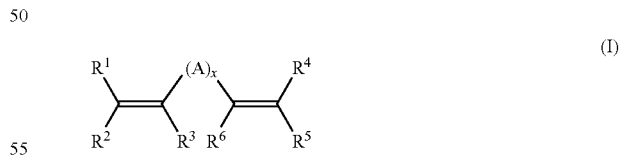

in which:

each A is independently a CR$^7$R$^8$ radical where one of the A radicals may be oxygen, sulphur, an NR$^9$ group or an SiR$^{10}$R$^{11}$ group, or where the A radicals may be a constituent of a 5- to 20-membered ring system, x is an integer from 2 to 4, and each R$^1$ to R$^{11}$ is independently selected from R, OR, halogen, CN, NO$_2$, NR$_2$, C(O)R, C(O)OR, OC(O)R, CONR$_2$, NHCO$_2$R, NHCOR, CH═CH—CO$_2$R, Si(R)$_3$, Si(OR)$_3$, SiR(OR)$_2$, SiR$_2$(OR), SO$_3$R, SO$_2$R, SOR, SR, PR$_2$, POR$_2$, PO$_3$H, PO(OR)$_2$, in which R is a hydrogen atom, a substituted or unsubstituted C$_{1-10}$-alkyl radical, a substituted or unsubstituted, mono- or polyunsaturated C$_{1-10}$-alkenyl radical, or a substituted or unsubstituted, optionally heteroatom-containing C$_{5-10}$-aryl radical, and the substituents on the alkyl radical or the alkenyl radical are selected from halogen, O—C$_{1-10}$-alkyl, phenyl, O-phenyl, OH, NH$_2$ and halogenated C$_{1-10}$-alkyl, and the substituents on the aryl radical are selected from halogen, C$_{1-10}$-alkyl, O—C$_{1-10}$-alkyl, phenyl, O-phenyl, OH, NH$_2$ and halogenated C$_{1-10}$-alkyl, where R$^2$ and R$^3$ and/or R$^5$ and R$^6$ together with the carbon atoms bonded thereto may be a constituent of a 5- to 7-membered, optionally heteroatom-containing ring.

In a further embodiment, the invention relates to a process for preparing a Palladium(0) compound, comprising reaction of a palladium compound with one or more compounds of the general formula II in the presence of a base:

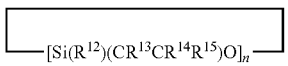
(II)

in which:

n is an integer from 3 to 20, each R$^3$ to R$^{15}$ is independently selected from R, OR, halogen, CN, NO$_2$, NR$_2$, C(O)R, C(O)OR, OC(O)R, CONR$_2$, NHCO$_2$R, NHCOR, CH=CH—CO$_2$R, Si(R)$_3$, Si(OR)$_3$, SiR(OR)$_2$, SiR$_2$(OR), SO$_3$R, SO$_2$R, SOR, SR, PR$_2$, POR$_2$, PO$_3$H, PO(OR)$_2$, in which R is hydrogen, a substituted or unsubstituted C$_{1-10}$-alkyl radical, a substituted or unsubstituted, mono- or polyunsaturated C$_{1-10}$-alkenyl radical, or a substituted or unsubstituted, optionally heteroatom-containing C$_{5-10}$-aryl radical, and the substituents on the alkyl radical or the alkenyl radical are selected from halogen, O—C$_{1-10}$-alkyl, phenyl, O-phenyl, OH, NH$_2$ and halogenated C$_{1-10}$-alkyl, and the substituents on the aryl radical are selected from halogen, C$_{1-10}$-alkyl, O—C$_{1-10}$-alkyl, phenyl, O-phenyl, OH, NH$_2$ and halogenated C$_{1-10}$-alkyl, where R$^{13}$ and R$^{14}$ together with the carbon atoms bonded thereto may be a constituent of a 5- to 7-membered, optionally heteroatom-containing ring, and each R$^{12}$ is independently selected from hydrogen, a hydroxyl group, a substituted or unsubstituted C$_{1-10}$-alkyl radical (in particular an unsubstituted or halogenated C$_{1-10}$-alkyl radical), an —O—C$_{1-10}$-alkyl radical (where the alkyl radical may be substituted or unsubstituted; in particular an unsubstituted or halogenated-O—C$_{1-10}$-alkyl radical), a substituted or unsubstituted, mono- or polyunsaturated C$_{1-10}$-alkenyl radical or a substituted or unsubstituted, optionally heteroatom-containing C$_{5-10}$-aryl radical, where the substituents are as defined for R$^{13}$ and R$^{15}$.

In yet a further embodiment, the invention relates to a process for preparing a Palladium(0) compound, comprising reaction of a palladium compound with one or more compounds of the general formula III in the presence of a base:

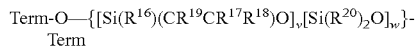
(III)

in which v and w are each independently 0 or an integer of from 1 to 1000 and v+w is from 0 to 1000, each R$^{16}$ is independently selected from a hydrogen atom, a hydroxyl group, a substituted or unsubstituted C$_{1-10}$-alkyl radical (in particular an unsubstituted or halogenated C$_{1-10}$-alkyl radical), an —O—C$_{1-10}$-alkyl radical (where the alkyl radical may be substituted or unsubstituted; in particular an unsubstituted or halogenated —O—C$_{1-10}$-alkyl radical), a substituted or unsubstituted, mono- or polyunsaturated C$_{1-10}$-alkenyl radical or a substituted or unsubstituted, optionally heteroatom-containing C$_{5-10}$-aryl radical, where the substituents are as defined for R$^{17}$ and R$^{19}$, each R$^{17}$ to R$^{19}$ is independently selected from R, OR, halogen, CN, NO$_2$, NR$_2$, C(O)R, C(O)OR, OC(O)R, CONR$_2$, NHCO$_2$R, NHCOR, CH=CH—CO$_2$R, Si(R)$_3$, Si(OR)$_3$, SiR(OR)$_2$, SiR$_2$(OR), SO$_3$R, SO$_2$R, SOR, SR, PR$_2$, POR$_2$, PO$_3$H, PO(OR)$_2$, in which R is hydrogen, a substituted or unsubstituted C$_{1-10}$-alkyl radical, a substituted or unsubstituted, mono- or polyunsaturated C$_{1-10}$-alkenyl radical, or a substituted or unsubstituted, optionally heteroatom-containing C$_{5-10}$-aryl radical, and the substituents on the alkyl radical or the alkenyl radical are selected from halogen, O—C$_{1-10}$-alkyl, phenyl, O-phenyl, OH, NH$_2$ and halogenated C$_{1-10}$-alkyl, and the substituents on the aryl radical are selected from halogen, C$_{1-10}$-alkyl, O—C$_{1-10}$-alkyl, phenyl, O-phenyl, OH, NH$_2$ and halogenated C$_{1-10}$-alkyl, where R$^{17}$ and R$^{19}$ together with the carbon atoms bonded thereto may be a constituent of a 5- to 7-membered, optionally heteroatom-containing ring, each R$^{20}$ is independently selected from hydrogen, a hydroxyl group, a substituted or unsubstituted C$_{1-10}$-alkyl radical (in particular an unsubstituted or halogenated C$_{1-10}$-alkyl radical), an —O—C$_{1-10}$-alkyl radical (where the alkyl radical may be substituted or unsubstituted in particular an unsubstituted or halogenated —O—C$_{1-10}$-alkyl radical), a substituted or unsubstituted, mono- or polyunsaturated C$_{1-10}$-alkenyl radical, or a substituted or unsubstituted, optionally heteroatom-containing C$_{5-10}$-aryl radical, where the substituents are as defined for R$^{17}$ and R$^{19}$, and each Term radical is independently (R$^{16}$)$_2$(CR$^{17}$R$^{18}$CR$^{19}$)Si— or (R$^{16}$)$_3$Si—.

Surprisingly, the above-described processes, unlike the processes known to date, can be carried out at temperatures above 0° C. In addition, the reaction does not have to be carried out with exclusion of air or with dried solvents.

In the palladium(0) compounds, palladium is present as palladium(0). The oxidation state of palladium in the compounds can be determined by known processes, for example by reacting with uncharged ligands (for example phosphines), isolating and characterizing the resulting compound with NMR, or by concentrating the solution by evaporation and determining the oxidation state by means of XPS.

Palladium Compound

The palladium compound used as the starting compound is not particularly restricted. It may be used either in the form of solids or in the form of aqueous or hydrochloric acid solutions. Preference is given to using palladium compounds having palladium in the +2 or +4 oxidation state. Examples thereof are PdX$_2$, PdX$_4$, M$_2$PdX$_4$, M$_2$PdX$_6$, (NH$_3$)$_2$PdX$_2$ and [Pd(NH$_3$)$_4$]X$_2$, where M is a cation (e.g.: a hydrogen atom, an alkali metal (in particular Na$^+$ or K$^+$) or NR*$_4^+$ (R*=hydrogen, C$_{1-4}$alkyl)) and X is an anion (e.g.: halogen (in particular chlorine), NO$_3^-$). Particularly preferred palladium compounds are PdCl$_2$, PdCl$_4$, Pd(NO$_3$)$_2$, [Pd(NH$_3$)$_4$]Cl$_2$, (NH$_3$)$_2$PdCl$_2$, H$_2$PdCl$_4$, H$_2$PdCl$_6$, Na$_2$PdCl$_4$, Na$_2$PdCl$_6$, K$_2$PdCl$_4$ and K$_2$PdCl$_6$.

Ligand of the General Formula I

The palladium compound is reacted with one or more compounds of the general formula I

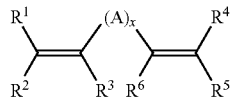
(I)

Each A is independently a $CR^7R^8$ radical where one of the A radicals may be oxygen, sulphur, an $NR^9$ group or an $SiR^{10}R^{11}$ group, or where the A radicals may be a constituent of a 5- to 20-membered ring system.

x is an integer of from 2 to 4.

Each $R^1$ to $R^{11}$ is independently selected from R, OR, halogen, CN, $NO_2$, $NR_2$, C(O)R, C(O)OR, OC(O)R, $CONR_2$, $NHCO_2R$, NHCOR, CH=CH—$CO_2R$, $Si(R)_3$, $Si(OR)_3$, $SiR(OR)_2$, $SiR_2(OR)$, $SO_3R$, $SO_2R$, SOR, SR, $PR_2$, $POR_2$, $PO_3H$, $PO(OR)_2$, in which R is hydrogen, a substituted or unsubstituted $C_{1-10}$-alkyl radical, a substituted or unsubstituted, mono- or polyunsaturated $C_{1-10}$-alkenyl radical, or a substituted or unsubstituted, optionally heteroatom-containing $C_{5-10}$-aryl radical, and the substituents on the alkyl radical or the alkenyl radical are selected from halogen, O—$C_{1-10}$-alkyl, phenyl, O-phenyl, OH, $NH_2$ and halogenated $C_{1-10}$-alkyl, and the substituents on the aryl radical are selected from halogen, $C_{1-10}$-alkyl, O—$C_{1-10}$-alkyl, phenyl, O-phenyl, OH, $NH_2$ and halogenated $C_{1-10}$-alkyl, where $R^2$ and $R^3$ and/or $R^5$ and $R^6$ together with the carbon atoms bonded thereto may be a constituent of a 5- to 7-membered, optionally heteroatom-containing ring.

Examples of heteroatom-containing rings are rings which derive from the following structures: thiophenes, furans, pyrans, pyrroles and the like. Other rings are likewise possible.

In a preferred embodiment, $R^1$ to $R^6$ are each independently hydrogen atoms, $C_{1-4}$-alkyl radicals or halogenated $C_{1-4}$-alkyl radicals; $R^1$ to $R^6$ are more preferably hydrogen atoms.

In a further preferred embodiment, $R^7$ and $R^8$ are preferably each independently hydrogen atoms, $C_{1-4}$-alkyl radicals or halogenated $C_{1-4}$-alkyl radicals; $R^7$ and $R^8$ are more preferably hydrogen atoms.

In yet a further embodiment, $R^9$ is preferably independently a hydrogen atom, a $C_{1-4}$-alkyl radical, a halogenated $C_{1-4}$-alkyl radical, a —C(O)—$C_{1-4}$ alkyl radical or a halogenated —C(O)—$C_{1-4}$ alkyl radical.

In a further embodiment, $R^{10}$ and $R^{11}$ are each independently selected from a hydroxyl group, a $C_{1-4}$ alkyl radical, an —O—$C_{1-4}$ alkyl radical, a halogenated $C_{1-4}$-alkyl radical or a halogenated —O—$C_{1-4}$-alkyl radical. $R^{10}$ and $R^{11}$ are more preferably each independently a $C_{1-4}$-alkyl radical or a halogenated $C_{1-4}$-alkyl radical.

R is preferably a hydrogen atom, a $C_{1-4}$-alkyl radical or a halogenated $C_{1-4}$-alkyl radical.

Halogens refer to fluorine, chlorine, bromine and iodine, preferably fluorine and chlorine. The radicals substituted by them may be mono- or polysubstituted, preferably perhalogenated.

The compounds of the formula I are preferably symmetrical.

In one embodiment, the -(A)$_x$-group is preferably a group of the formula —$CH_2$—X—$CH_2$— and —X— is selected from —O—, —S—, —$SiR_2$—, —NR— and —NC(O)R, where R is a hydrogen atom, a $C_{1-4}$-alkyl radical, a halogenated $C_{1-4}$-alkyl radical, an O—$C_{1-4}$-alkyl radical, a halogenated O—$C_{1-4}$-alkyl radical, a $C_{1-4}$-alkenyl radical or an optionally heteroatom-containing $C_{5-6}$-aryl radical.

Illustrative examples of compounds of the general formula I are 1,5-hexadiene, 1,6-heptadiene and 1,7-octadiene. Further compounds which may serve as illustration are diallyl ether, diallylamine, diallyl-methylamine, diallylethylamine, N-acetyldiallylamine, diallyl sulphide, diallylsilane, diallyldimethylsilane, difurfuryl ether, difurfurylamine, bis(thiophen-2-yl-methyl)amine, difurfuryl sulphide and 1,3-divinyl-benzene.

Ligand of the General Formula II

The present invention further provides a process for preparing a palladium(0) compound, comprising reaction of a palladium compound with one or more compounds of the general formula II in the presence of a base:

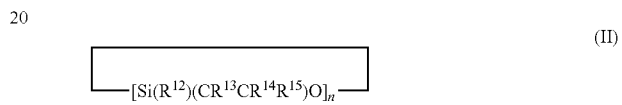
(II)

n is an integer from 3 to 20; n is preferably an integer from 3 to 6.

Each $R^{13}$ to $R^{15}$ is independently selected from R, OR, halogen, CN, $NO_2$, $NR_2$, C(O)R, C(O)OR, OC(O)R, $CONR_2$, $NHCO_2R$, NHCOR, CH=CH—$CO_2R$, $Si(R)_3$, $Si(OR)_3$, $SiR(OR)_2$, $SiR_2(OR)$, $SO_3R$, $SO_2R$, SOR, SR, $PR_2$, $POR_2$, $PO_3H$, $PO(OR)_2$, in which R is hydrogen, a substituted or unsubstituted $C_{1-10}$-alkyl radical, a substituted or unsubstituted, mono- or polyunsaturated $C_{1-10}$-alkenyl radical, or a substituted or unsubstituted, optionally heteroatom-containing $C_{5-10}$-aryl radical, and the substituents on the alkyl radical or the alkenyl radical are selected from halogen, O—$C_{1-10}$-alkyl, phenyl, O-phenyl, OH, $NH_2$ and halogenated $C_{1-10}$-alkyl, and the substituents on the aryl radical are selected from halogen, $C_{1-10}$-alkyl, O—$C_{1-10}$-alkyl, phenyl, O-phenyl, OH, $NH_2$ and halogenated $C_{1-10}$-alkyl, where $R^{13}$ and $R^{14}$ together with the carbon atoms bonded thereto may be a constituent of a 5- to 7-membered, optionally heteroatom-containing ring.

Examples of heteroatom-containing rings are rings which derive from the following structures: thiophenes, furans, pyrans, pyrroles and the like. Other rings are likewise possible.

In a preferred embodiment, $R^{13}$ to $R^{15}$ are each independently hydrogen atoms, $C_{1-4}$-alkyl radicals or halogenated $C_{1-4}$-alkyl radicals; $R^{13}$ to $R^{15}$ are more preferably hydrogen atoms.

Each $R^{12}$ is independently selected from hydrogen, a hydroxyl group, a substituted or unsubstituted $C_{1-10}$-alkyl radical (in particular an unsubstituted or halogenated $C_{1-10}$-alkyl radical), an —O—$C_{1-10}$-alkyl radical (where the alkyl radical may be substituted or unsubstituted; in particular an unsubstituted or halogenated —O—$C_{1-10}$-alkyl radical), a substituted or unsubstituted, mono- or polyunsaturated $C_{1-10}$-alkenyl radical or a substituted or unsubstituted, optionally heteroatom-containing $C_{5-10}$-aryl radical. The substituents are each as defined for $R^{13}$ to $R^{15}$. Each $R^{12}$ is preferably selected independently from a hydroxyl group, a $C_{1-4}$-alkyl radical, an —O—$C_{1-4}$-alkyl radical, a halogenated $C_{1-4}$-alkyl radical or a halogenated —O—$C_{1-4}$-alkyl radical. Each $R^{12}$ is more preferably each independently a $C_{1-4}$-alkyl radical or a halogenated $C_{1-4}$-alkyl radical.

R is preferably a hydrogen atom, a $C_{1-4}$-alkyl radical or a halogenated $C_{1-4}$-alkyl radical.

Halogens refer to fluorine, chlorine, bromine and iodine, preferably fluorine and chlorine. The radicals substituted with them may be mono- or polysubstituted, preferably perhalogenated.

Ligand of the General Formula III

The present invention also provides a process for preparing a palladium(0) compound, comprising reaction of a palladium compound with one or more compounds of the general formula III in the presence of a base:

$$\text{Term-O---}\{[Si(R^{16})(CR^{19}CR^{17}R^{18})O]_v[Si(R^{20})_2O]_w\}\text{-Term} \qquad (III).$$

This formula encompasses both compounds in which the $[Si(R^{16})(CR^{19}CR^{17}R^{18})O]$ and $[Si(R^{20})_2O]$ units occur in blocks and compounds in which individual $[Si(R^{16})(CR^{19}CR^{17}R^{18})O]$ and $[Si(R^{20})_2O]$ units are distributed randomly in the chain. Mixed forms are likewise possible.

v and w are each independently 0 or an integer from 1 to 1000 and v+w is from 0 to 1000. v and w are preferably each independently 0 or an integer from 1 to 100 and v and w is from 0 to 100; more preferably v and w are each independently 0 or an integer from 1 to 20 and v+w is from 0 to 20.

Each $R^{16}$ is independently selected from a hydrogen atom, a hydroxyl group, a substituted or unsubstituted $C_{1-10}$-alkyl radical (in particular an unsubstituted or halogenated $C_{1-10}$-alkyl radical), an —O—$C_{1-10}$-alkyl radical (where the alkyl radical may be substituted or unsubstituted; in particular an unsubstituted or halogenated —O—$C_{1-10}$-alkyl radical), a substituted or unsubstituted, mono- or polyunsaturated $C_{1-10}$-alkenyl radical, or a substituted or unsubstituted, optionally heteroatom-containing $C_{5-10}$-aryl radical. The substituents are each as defined for $R^{17}$ and $R^{19}$. Each $R^{16}$ is preferably each independently selected from a hydroxyl group, a $C_{1-4}$-alkyl radical, an —O—$C_{1-4}$-alkyl radical, a halogenated $C_{1-4}$-alkyl radical or a halogenated —O—$C_{1-4}$-alkyl-radical. Each $R^{16}$ is more preferably each independently an $C_{1-4}$-alkyl radical or a halogenated $C_{1-4}$-alkyl radical.

Each $R^{17}$ to $R^{19}$ is independently selected from R, OR, halogen, CN, $NO_2$, $NR_2$, C(O)R, C(O)OR, OC(O)R, $CONR_2$, $NHCO_2R$, NHCOR, CH=CH—$CO_2R$, $Si(R)_3$, $Si(OR)_3$, $SiR(OR)_2$, $SiR_2(OR)$, $SO_3R$, $SO_2R$, SOR, SR, $PR_2$, $POR_2$, $PO_3H$, $PO(OR)_2$, in which R is an hydrogen, a substituted or unsubstituted $C_{1-10}$-alkyl radical, a substituted or unsubstituted, mono- or polyunsaturated $C_{1-10}$-alkenyl radical, or a substituted or unsubstituted, optionally heteroatom-containing $C_{5-10}$-aryl radical, and the substituents on the alkyl radical or the alkenyl radical are selected from halogen, O—$C_{1-10}$-alkyl, phenyl, O-phenyl, OH, $NH_2$ and halogenated $C_{1-10}$-alkyl, and the substituents on the aryl radical are selected from halogen, $C_{1-10}$-alkyl, O—$C_{1-10}$-alkyl, phenyl, O-phenyl, OH, $NH_2$ and halogenated $C_{1-10}$-alkyl, where $R^{17}$ and $R^{19}$ together with the carbon atoms bonded thereto may be a constituent of a 5- to 7-membered, optionally heteroatom-containing ring.

The examples of heteroatom-containing rings are rings which derive from the following structures: thiophenes, furans, pyrans, pyrroles and the like. Other rings are likewise possible.

In a preferred embodiment, $R^{17}$ to $R^{19}$ are each independently hydrogen atoms, halogens, $C_{1-4}$-alkyl radicals or halogenated $C_{1-4}$-alkyl radicals; $R^{17}$ to $R^{19}$ are more preferably hydrogen atoms.

Each $R^{20}$ is independently selected from a hydrogen atom, a hydroxyl group, a substituted or unsubstituted $C_{1-10}$-alkyl radical (in particular an unsubstituted or halogenated $C_{1-10}$-alkyl radical), an —O—$C_{1-10}$-alkyl radical (where the alkyl radical may be substituted or unsubstituted; in particular an unsubstituted or halogenated —O—$C_{1-10}$-alkyl radical), a substituted or unsubstituted, mono- or polyunsaturated $C_{1-10}$-alkenyl radical, or a substituted or unsubstituted, optionally heteroatom-containing $C_{5-10}$-aryl radical. The substituents are each as defined for $R^{17}$ and $R^{19}$. Each $R^{20}$ is preferably independently selected from a hydrogen atom, a hydroxyl group, a $C_{1-4}$-alkyl radical, an —O—$C_{1-4}$-alkyl radical, a halogenated $C_{1-4}$-alkyl radical or a halogenated —O—$C_{1-4}$-alkyl radical. Each $R^{20}$ is more preferably independently a hydrogen atom, a $C_{1-4}$-alkyl radical or a halogenated $C_{1-4}$-alkyl radical.

Each Term radical is independently $(R^{16})_2(CR^{17}R^{18}CR^{19})Si$— or $(R^{16})_3Si$—. The unsaturated radical is preferably $(R^{16})_2(CR^{17}R^{18}CR^{19})Si$—.

R is preferably a hydrogen atom, a $C_{1-4}$-alkyl radical or a halogenated $C_{1-4}$-alkyl radical.

Halogens refer to fluorine, chlorine, bromine and iodine, preferably fluorine and chlorine. The radicals substituted with them may be mono- or polysubstituted, preferably perhalogenated.

In a preferred embodiment, w is 0. In this case, the compounds of the general formula (III) have the following form:

$$\text{Term-O---}[Si(R^{16})(CR^{19}CR^{17}R^{18})O]_v\text{-Term}$$

where $R^{16}$ to $R^{19}$, Term and v are each as defined above.

Illustrative examples of compounds of the general formulae II and III are divinyldisiloxane, 1,1,3,3-tetramethyl-1,3-divinyldisiloxane, 1,1,3,3-tetramethyl-1,3-dithien-2-yldisiloxane, 1,1,3,3-tetramethoxy-1,3-divinyldisiloxane, 1,3-dimethyl-1,3-divinyldisiloxane-diol, 1,3,5,7-tetravinyl-1,3,5,7-tetramethylcyclotetra-siloxane and 1,3,5-trimethyl-1,3,5-trivinylcyclo-trisiloxane. Particular preference is given to 1,1,3,3-tetramethyl-1,3-divinyldisiloxane, 1,3,5,7-tetravinyl-1,3,5,7-tetramethylcyclotetrasiloxane and 1,3,5-trimethyl-1,3,5-trivinylcyclotrisiloxane.

It goes without saying that the palladium compound can be reacted with mixtures of the compounds of the general formula I, II and III. In the reaction of the palladium compound with one or more of the compounds of the general formula I, II and III, preference is given to no further ligands in addition to the compounds of the general formula I, II and III during the reaction.

Base

The palladium compound is reacted with one or more compounds of the general formula I, II or III in the presence of a base. In the context of the invention, "base" refers to inorganic and organic (preferably inorganic) bases, but not organometallic bases. The bases should not decompose in water. Suitable bases are, for example, salts of Bronsted acids. Preference is given to using carbonates, hydrogencarbonates, acetates, formates, ascorbates, oxalates and hydroxides. These may be used in the form of their ammonium ($NR_4^+$ where R=H or $C_{1-4}$-alkyl), alkali metal (for example sodium or potassium) and alkaline earth metal salts.

Solvent

The components are reacted typically in a solvent. The solvents are not particularly restricted. Examples of possible solvents are water, alcohols, hydrocarbons (e.g. aromatic hydrocarbons such as benzene and toluene or aliphatic hydrocarbons such as pentane, hexane and heptane), open-chain or cyclic ethers, amides and esters. However, preference is given to water, $C_{1-6}$ alcohols (e.g. $C_{1-4}$ alcohols such as methanol, ethanol, propanol and butanol) and $C_{2-6}$ ethers as solvents. Mixtures of these solvents may likewise be used.

Reducing Agent

In order to accelerate the reaction or achieve very substantial conversion, the reaction may optionally be effected in the presence of a reducing agent. Suitable reducing agents are those which, compared to the palladium compound used, have a lower redox potential under the selected reaction conditions. For example, formic acid and salts thereof, oxalic acid and salts thereof, hydrazine, glucose, ascorbic acid or formaldehyde can be used. Instead of using a separate reducing agent, it is likewise possible to use a solvent which has reducing properties.

Performance of the Process

In one possible embodiment of the process according to the invention, the palladium compound and the compound of the general formula I, II or III is preferably dissolved in a solvent and the base is suspended in the solution. The reactants are reacted with one another. To this end, the reactants are introduced into a reactor and stirred. The reaction may be effected at a temperature of −78° C. to +200° C., preferably of −10° C. to +100° C. and more preferably of 0° C. to +50° C. The pressure is generally 0.1 mbar to 100 bar, preferably 0.2 to 2 bar. Particular preference is given to ambient pressure ±0.2 bar. The reaction time is commonly 5 minutes to 1 week, preferably 5 minutes to 24 hours, more preferably 30 minutes to 24 hours. As mentioned above, it is not necessary to work with exclusion of air, which is particularly advantageous for the industrial-scale application of the process according to the invention.

Based on 1 equivalent of palladium in the form of the compound used, 1 to 100 equivalents, preferably 3 to 100 equivalents, more preferably 8 to 20 equivalents, of the compound of the general formula I, II or III are used. The base is used in an amount of 1 to 100 equivalents preferably of 2 to 100 equivalents, more preferably of 2.5 to 10 equivalents, based on 1 equivalent of palladium. If present, the reducing agent may be added in an amount of 1 to 100 equivalents based on 1 equivalent of palladium. Instead of using a separate reducing agent, it is likewise possible to use a solvent which has reducing properties. In this case, the amount of the reducing agent (solvent) is not particularly restricted, but rather it can be used in any excess based on 1 equivalent of palladium.

The palladium(0) compounds may be used as such after the reaction. However, it is possible to purify and/or to concentrate the solutions before use. Useful purification steps are, for example, the filtering-off of by-products, the drying of the solution (for example over molecular sieves or $MgSO_4$) or the purification over activated carbon. The solution may be concentrated, for example, by distillation.

The palladium(0) compounds prepared by the process according to the invention are also storage-stable and can be handled under air, generally at temperatures up to 30° C., in some cases up to 60° C. and higher. They typically have a metal content of 0.01% by weight to 40% by weight, preferably of 0.01% by weight to 30% by weight, more preferably of 0.01% by weight to 20% by weight, and a total halogen content of not more than 5% by weight, preferably not more than 2% by weight, more preferably not more than 1% by weight.

The palladium(0) compounds may, either alone or as a mixture, be used as a precursor for catalysts for organic chemistry reactions, by mixing them with a ligand, for example phosphines, phosphites, phosphonites, amines, alkenes, thioethers, alkynes or carbenes, each of which may also be generated in situ. This mixture may be used directly as a catalyst, or the resulting complex may be obtained in substance by customary processes from the mixture.

The inventive palladium(0) compounds may, either alone or as a mixture, also be used directly without using additional ligands as a catalyst precursor in organic chemistry reactions.

The examples which follow are intended to further illustrate the invention. However, the invention is not restricted to these illustrative embodiments, but rather is defined by the claims.

EXAMPLES

General Method for the Synthesis of Palladium(0) Compounds

One equivalent of sodium tetrachloropalladate was dissolved in methanol. To this solution were added 8 equivalents of sodium hydrogencarbonate and 10 equivalents of a compound of the general formula I. The solution was stirred for 4 hours. The methanol was distilled off and the residue stirred over a desiccant and activated carbon. The solids were filtered off and the filtrate was concentrated by distillation. Depending on the distillation conditions, stable palladium solutions having palladium contents of 0.01 to 20% by weight were obtained.

According to this method, reaction mixtures were prepared with the di- to tetraenes specified in Table 1.

The palladium and chlorine content was determined by means of ICP-OES after digestion or by Wickbold combustion.

Method for the Synthesis of Phosphine-Diene-Pd(0) Complexes

One palladium equivalent of the palladium solution obtained from the reaction of 1,1,3,3-tetramethyl-1,3-divinyldisiloxane was admixed with one equivalent of a 5% by weight ethereal tricyclohexylphosphine solution. The resulting precipitate is filtered off and dried. The product was identified by means of $^1H$, $^{31}P$ and $^{13}C$ NMR spectroscopy as tricyclohexylphosphine-(1,1,3,3-tetramethyl-1,3-divinyldisiloxane)-Pd(0) complex.

TABLE 1

| Diene component | Yield [%] | Pd content [%] | Cl content [%] |
|---|---|---|---|
| Ex. 1 Diallyl ether | 81 | 7.9 | 0.11 |
| Ex. 2 1,5-Hexadiene | 69 | 3.3 | 0.5 |
| Ex. 3 1,7-Octadiene | 78 | 5.2 | 0.11 |
| Ex. 4 Diallylamine | 84 | 8.0 | 0.1 |
| Ex. 5 Diallylmethylamine | 87 | 8.0 | 0.09 |
| Ex. 6 1,1,3,3-Tetramethyl-1,3-divinyl-disiloxane | 91 | 18.6 | 0.02 |
| Ex. 7 1,3,5,7-Tetravinyl-1,3,5,7-tetramethylcyclotetrasiloxane | 94 | 2.3 | 0.03 |
| Ex. 8 1,3,5,-Trimethyl-1,3,5-trivinylcyclo-trisiloxane | 91 | 10.0 | 0.02 |

The invention claimed is:

1. Process for preparing a Palladium(0) compound, comprising reaction of a palladium compound with one or more compounds of the general formula I in the presence of a base:

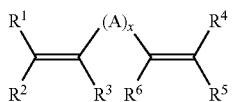

(I)

in which:
each A is independently a $CR^7R^8$-radical where one of the A radicals may be oxygen, sulphur, an $NR^9$ group or an $SiR^{10}R^{11}$ group, or where the A radicals may be a constituent of a 5- to 20-membered ring system,
x is an integer from 2 to 4, and
each $R^1$ to $R^{11}$ is independently selected from R, OR, halogen, CN, $NO_2$, $NR_2$, C(O)R, C(O)OR, OC(O)R, $CONR_2$, $NHCO_2R$, NHCOR, $CH=CH-CO_2R$, $Si(R)_3$, $Si(OR)_3$, $SiR(OR)_2$, $SiR_2(OR)$, $SO_3R$, $SO_2R$, SOR, SR, $PR_2$, $POR_2$, $PO_3H$, $PO(OR)_2$, in which R is a hydrogen atom, a substituted or unsubstituted $C_{1-10}$-alkyl radical, a substituted or unsubstituted, mono- or polyunsaturated $C_{1-10}$-alkenyl radical, or a substituted or unsubstituted, optionally heteroatom-containing $C_{5-10}$-aryl radical, and the substituents on the alkyl radical or the alkenyl radical are selected from halogen, $O-C_{1-10}$-alkyl, phenyl, O-phenyl, OH, $NH_2$ and halogenated $C_{1-10}$-alkyl, and the substituents on the aryl radical are selected from halogen, $C_{1-10}$-alkyl, $O-C_{1-10}$-alkyl, phenyl, O-phenyl, OH, $NH_2$ and halogenated $C_{1-10}$-alkyl, where $R^2$ and $R^3$ and/or $R^5$ and $R^6$ together with the carbon atoms bonded thereto may be a constituent of a 5- to 7-membered, optionally heteroatom-containing ring.

2. Process according to claim 1, wherein x is 3.

3. Process according to claim 1, wherein $R^1$ to $R^6$ are each hydrogen atoms.

4. Process according to claim 1, wherein $-(A)_x-$ is a group of the formula $-CH_2-X-CH_2-$ and $-X-$ is selected from $-O-$, $-S-$, $-SiR_2-$, $-NR-$ and $-NC(O)R$, and R is hydrogen, a $C_{1-4}$-alkyl radical or a halogenated $C_{1-4}$-alkyl.

5. Process according to claim 1, wherein the compound of the general formula I is selected from 1,5-hexadiene, 1,6-heptadiene and 1,7-octadiene.

6. Process according to claim 1, wherein the compound of the general formula I is selected from diallyl ether, diallylamine, diallylmethylamine, diallylethylamine, N-acetyldiallylamine, diallyl sulphide, diallylsilane, diallyldimethylsilane, difurfuryl ether, difurfurylamine, bis(thiophen-2-ylmethyl)amine, difurfuryl sulphide and 1,3-divinylbenzene.

7. Process for preparing a Palladium(0) compound, comprising reaction of a palladium compound with one or more compounds of the general formula II in the presence of a base:

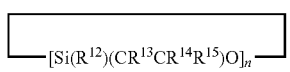

(II)

in which:
n is an integer from 3 to 20,
each $R^{13}$ to $R^{15}$ is independently selected from R, OR, halogen, CN, $NO_2$, $NR_2$, C(O)R, C(O)OR, OC(O)R, $CONR_2$, $NHCO_2R$, NHCOR, $CH=CH-CO_2R$, $Si(R)_3$, $Si(OR)_3$, $SiR(OR)_2$, $SiR_2(OR)$, $SO_3R$, $SO_2R$, SOR, SR, $PR_2$, $POR_2$, $PO_3H$, $PO(OR)_2$, in which R is hydrogen, a substituted or unsubstituted $C_{1-10}$-alkyl radical, a substituted or unsubstituted, mono- or polyunsaturated $C_{1-10}$-alkenyl radical, or a substituted or unsubstituted, optionally heteroatom-containing $C_{5-10}$-aryl radical, and the substituents on the alkyl radical or the alkenyl radical are selected from halogen, $O-C_{1-10}$-alkyl, phenyl, O-phenyl, OH, $NH_2$ and halogenated $C_{1-10}$-alkyl, and the substituents on the aryl radical are selected from halogen, $C_{1-10}$-alkyl, $O-C_{1-10}$-alkyl, phenyl, O-phenyl, OH, $NH_2$ and halogenated $C_{1-10}$-alkyl, where $R^{13}$ and $R^{14}$ together with the carbon atoms bonded thereto may be a constituent of a 5- to 7-membered, optionally heteroatom-containing ring, and
each $R^{12}$ is independently selected from hydrogen, a hydroxyl group, a substituted or unsubstituted $C_{1-10}$-alkyl radical, an $-O-C_{1-10}$-alkyl radical (where the alkyl radical may be substituted or unsubstituted), a substituted or unsubstituted, mono- or polyunsaturated $C_{1-10}$-alkenyl radical or a substituted or unsubstituted, optionally heteroatom-containing $C_{5-10}$-aryl radical, where the substituents are as defined for $R^{13}$ and $R^{15}$.

8. Process according to claim 7, wherein n is an integer from 3 to 6 and each $R^{12}$ is independently a $C_{1-4}$-alkyl radical or a halogenated $C_{1-4}$-alkyl radical.

9. Process for preparing a Palladium(0) compound, comprising reaction of a palladium compound with one or more compounds of the general formula III in the presence of a base:

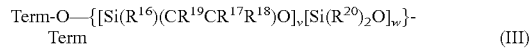

(III)

in which
v and w are each independently 0 or an integer of from 1 to 1000 and v+w is from 0 to 1000,
each $R^{16}$ is independently selected from hydrogen, a hydroxyl group, a substituted or unsubstituted $C_{1-10}$-alkyl radical, an $-O-C_{1-10}$-alkyl radical (where the alkyl radical may be substituted or unsubstituted), a substituted or unsubstituted, mono- or polyunsaturated $C_{1-10}$-alkenyl radical or a substituted or unsubstituted, optionally heteroatom-containing $C_{5-10}$-aryl radical, where the substituents are as defined for $R^{17}$ and $R^{19}$,
each $R^{17}$ to $R^{19}$ is independently selected from R, OR, halogen, CN, $NO_2$, $NR_2$, C(O)R, C(O)OR, OC(O)R, $CONR_2$, $NHCO_2R$, NHCOR, $CH=CH-CO_2R$, $Si(R)_3$, $Si(OR)_3$, $SiR(OR)_2$, $SiR_2(OR)$, $SO_3R$, $SO_2R$, SOR, SR, $PR_2$, $POR_2$, $PO_3H$, $PO(OR)_2$, in which R is a hydrogen atom, a substituted or unsubstituted $C_{1-10}$-alkyl radical, a substituted or unsubstituted, mono- or polyunsaturated $C_{1-10}$-alkenyl radical, or a substituted or unsubstituted, optionally heteroatom-containing $C_{5-10}$-aryl radical, and the substituents on the alkyl radical or the alkenyl radical are selected from halogen, $O-C_{1-10}$-alkyl, phenyl, O-phenyl, OH, $NH_2$ and halogenated $C_{1-10}$-alkyl, and the substituents on the aryl radical are selected from halogen, $C_{1-10}$-alkyl, $O-C_{1-10}$-alkyl, phenyl, O-phenyl, OH, $NH_2$ and halogenated $C_{1-10}$-alkyl, where $R^{17}$ and $R^{19}$ together with the carbon atoms bonded thereto may be a constituent of a 5- to 7-membered, optionally heteroatom-containing ring,
each $R^{20}$ is independently selected from hydrogen, a hydroxyl group, a substituted or unsubstituted $C_{1-10}$-alkyl radical, an $-O-C_{1-10}$-alkyl radical (where the alkyl radical may be substituted or unsubstituted), a substituted or unsubstituted, mono- or polyunsaturated $C_{1-10}$-alkenyl radical, or a substituted or unsubstituted, optionally heteroatom-containing $C_{5-10}$-aryl radical, where the substituents are as defined for $R^{17}$ and $R^{19}$, and each Term is independently $(R^{16})_2(CR^{17}R^{18}CR^{19})Si—$ or $(R^{16})_3Si—$.

10. Process according to claim 9, wherein the compound of the general formula (III) has the general formula:

Term-O—[Si($R^{16}$)($CR^{19}CR^{17}R^{18}$)O]$_v$-Term where $R^{16}$ to $R^{19}$, Term and v are each as defined in claim 9.

11. Process according to claim 7, wherein the compound of the general formula II or III is selected from divinyldisiloxane, 1,1,3,3-tetramethyl-1,3-divinyldisiloxane, 1,1,3,3-tetramethyl-1,3-dithien-2-yldisiloxane, 1,1,3,3-tetramethoxy-1,3-divinyldisiloxane, 1,3-dimethyl-1,3-divinyldisiloxanediol, 1,3,5,7-tetravinyl-1,3,5,7-tetramethylcyclotetrasiloxane and 1,3,5-trimethyl-1,3,5-trivinylcyclotrisiloxane.

12. Process according to claim 7, wherein the compound of the general formula II or III is selected from 1,1,3,3-tetramethyl-1,3-divinyldisiloxane, 1,3,5,7-tetravinyl-1,3,5,7-tetramethylcyclotetrasiloxane and 1,3,5-trimethyl-1,3,5-trivinylcyclotrisiloxane.

13. Process according to claim 1, wherein the palladium compound is selected from $PdX_2$, $PdX_4$, $M_2PdX_4$, $M_2PdX_6$, $(NH_3)_2PdX_2$ and $[Pd(NH_3)_4]X_2$, where M is a hydrogen atom, an alkali metal or $NR^*_4{}^+$ ($R^*$=hydrogen, $C_{1-4}$-alkyl) and X is a halogen or $NO_3{}^-$.

14. Process according to claim 13, wherein X is chlorine.

15. Process according to claim 1, wherein the reaction is effected in the presence of a solvent or solvent mixture.

16. Process according to claim 15, wherein the solvent is selected from water, $C_{1-6}$-alcohols and $C_{2-6}$-ethers and mixtures thereof.

17. Process according to claim 1, wherein the base is selected from alkali metal salts, alkaline earth metal salts and ammonium salts (ammonium as $NR_4{}^+$ where R=H or $C_{1-4}$-alkyl) of carbonates, hydrogencarbonates and hydroxides.

18. Process according to claim 1, also comprising a purification step.

19. Process according to claim 1, also comprising a concentration step.

20. Process according to claim 1, wherein the reaction of the palladium compound with one or more compounds of the general formula I, II or III is carried out in the presence of one or more ligands other than the compound of the general formula I, II or III.

21. Process according to claim 1, further comprising the reaction of the palladium compound with one or more ligands other than the compound of the general formula I, II or III.

22. Palladium(0) compound obtainable by a process according to claim 7, wherein the compound of the general formula II is 1,3,5,7-tetravinyl-1,3,5,7-tetramethylcyclotetrasiloxane.

* * * * *